US012290684B2

(12) United States Patent
Vu et al.

(10) Patent No.: US 12,290,684 B2
(45) Date of Patent: May 6, 2025

(54) WEARABLE SYSTEM FOR INTRA-EAR SENSING AND STIMULATING

(71) Applicant: THE REGENTS OF THE UNIVERSITY OF COLORADO, A BODY CORPORATE, Denver, CO (US)

(72) Inventors: Tam Vu, Boulder, CO (US); Robin Deterding, Boulder, CO (US); Farnoush Banaei-Kashani, Centennial, CO (US); Nhat Pham, Boulder, CO (US); Nam Ngoc Bui, Broomfield, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 467 days.

(21) Appl. No.: 17/642,621

(22) PCT Filed: Sep. 11, 2020

(86) PCT No.: PCT/US2020/050545
§ 371 (c)(1),
(2) Date: Mar. 11, 2022

(87) PCT Pub. No.: WO2021/050985
PCT Pub. Date: Mar. 18, 2021

(65) Prior Publication Data
US 2022/0339444 A1     Oct. 27, 2022

Related U.S. Application Data

(60) Provisional application No. 62/900,187, filed on Sep. 13, 2019.

(51) Int. Cl.
*A61N 1/36* (2006.01)
*A61B 5/00* (2006.01)
(Continued)

(52) U.S. Cl.
CPC ...... *A61N 1/36036* (2017.08); *A61B 5/02438* (2013.01); *A61B 5/369* (2021.01);
(Continued)

(58) Field of Classification Search
None
See application file for complete search history.

(56) References Cited

U.S. PATENT DOCUMENTS

| 5,549,655 A * | 8/1996 | Erickson | A61N 1/3601 |
| | | | 607/42 |
| 2005/0059870 A1 * | 3/2005 | Aceti | A61B 5/6815 |
| | | | 600/595 |

(Continued)

FOREIGN PATENT DOCUMENTS

WO    WO-2018027141 A1 *  2/2018  ............. A61B 5/374

OTHER PUBLICATIONS

International Search Report and Written Opinion received for PCT Patent Application No. PCT/US2020/050545 mailed on Nov. 30, 2020; 10 pages.

*Primary Examiner* — Mallika D Fairchild
(74) *Attorney, Agent, or Firm* — Workman Nydegger

(57) ABSTRACT

A computer system for intra-ear sensing and stimulating receives, health data, from an earbud sensor. The system repeatedly calculates an exponential moving average (EMA) of a moving window for the received health data. The system compares each calculated exponential moving average with a lower threshold value and an upper threshold value. The upper threshold value and the lower threshold value are determined based, at least in part, upon a saturation level (Continued)

associated within an amplifier performing the adaptive gain control. When the calculated exponential moving average is larger than the upper threshold, the system decreases a gain associated with the amplifier. When the calculated exponential moving average is smaller than the lower threshold, the system increases a gain associated with the amplifier.

11 Claims, 7 Drawing Sheets

(51) Int. Cl.
  *A61B 5/024* (2006.01)
  *A61B 5/369* (2021.01)
  *A61B 5/389* (2021.01)
  *A61B 5/398* (2021.01)
  *A61M 21/02* (2006.01)
  *A61N 1/05* (2006.01)

(52) U.S. Cl.
  CPC .............. *A61B 5/389* (2021.01); *A61B 5/398* (2021.01); *A61B 5/4094* (2013.01); *A61B 5/6817* (2013.01); *A61M 21/02* (2013.01); *A61N 1/0541* (2013.01)

(56) References Cited

U.S. PATENT DOCUMENTS

| | | | |
|---|---|---|---|
| 2014/0171775 A1* | 6/2014 | Kilsgaard | A61B 5/6817 600/379 |
| 2014/0288447 A1* | 9/2014 | Luna | A61B 5/6838 600/508 |
| 2019/0111261 A1* | 4/2019 | Glenn | A61B 5/291 |
| 2019/0209038 A1* | 7/2019 | Saab | A61B 5/38 |
| 2019/0247010 A1 | 8/2019 | Barnacka | |

* cited by examiner

WEARABLE SYSTEM FOR INTRA-EAR SENSING AND STIMULATING

CROSS-REFERENCE TO RELATED APPLICATIONS

This patent application is a nationalization of and claims priority to PCT Application No. PCT/US2020/050545 filed on 11 Sep. 2020 and entitled "A Wearable System for Intra-Ear Sensing and Stimulating", which claims priority to and the benefit of U.S. Provisional Patent Application Ser. No. 62/900,187 filed on 13 Sep. 2019 and entitled "A Wearable System for Intra-Ear Sensing and Stimulating". Each of the aforementioned applications is incorporated by reference herein in their entirety.

BACKGROUND

Computers and computing systems have affected nearly every aspect of modern living. Computers are generally involved in work, recreation, healthcare, transportation, entertainment, household management, etc. In recent years, wearable computing devices have experienced explosive market growth. This growth has been driven, at least in part, by the miniaturization of computing components and sensors.

Many conventional wearables computing devices integrate sensor technology to provide health information such as heart rate. This information can be continuously gathered by the wearable as the user goes through his or her normal daily activities. The ability to accurately gather additional health information and process the gathered information with miniaturized computing components and sensors presents several significant challenges in the art.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

At least one embodiment a system for intra-ear sensing and stimulating. The system comprises an earbud sensor. The earbud sensor further comprises a shape and size that is configured to extend, at least partially, into an ear canal of a user, and one or more of the following sensor components: an inertial measurement unit, an LED and photodiode, a microphone, a radio antenna, or a camera. The earbud sensor is configured to non-invasively measure various health information, including one or more of brain waves (EEG and electromagnetic fields generated by neural activities), eyes movements (EOG), facial muscle activities (EMG), heart rate, breathing rate, swallowing sound, ear canal pictures, and head motion from inside human ears.

Additionally or alternatively, an embodiment of the system includes a computer-implemented method, executed on one or more processors, for intra-ear sensing and stimulating. The method comprises receiving, health data, from an earbud sensor. The ear bud sensor comprises a shape and size that is configured to extend, at least partially, into an ear canal of a user, and one or more of the following sensor components: an inertial measurement unit, an LED and photodiode, a microphone, a radio antenna, or a camera. The method also includes repeatedly calculating an exponential moving average (EMA) of a moving window for the received health data. Further, the method includes comparing each calculated exponential moving average with a lower threshold value and an upper threshold value, wherein the upper threshold value and the lower threshold value are determined based, at least in part, upon a saturation level associated within an amplifier performing the adaptive gain control. When the calculated exponential moving average is larger than the upper threshold, the method includes decreasing a gain associated with the amplifier. When the calculated exponential moving average is smaller than the lower threshold, the method includes increasing a gain associated with the amplifier.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings described below.

DETAILED DESCRIPTION

Disclosed embodiments include a novel and light weight design of an ear-based wearable system which can non-invasively measure various health information such as brain waves (EEG), eyes movements (EOG), facial muscle activities (EMG), heart rate, breathing rate, swallowing sound, ear canal pictures, electromagnetic radiation and head motion from inside human ears. As used herein, "health information" comprises sensor readings relating to physiological aspects of the human user. In at least one embodiment, the system also provides automatic stimulation therapy to the user with acoustic, vibration, or non-invasive deep brain stimulation with a transcranial electrical field or a magnetic field based on the sensed health information in a closed-loop fashion.

Figure 1:
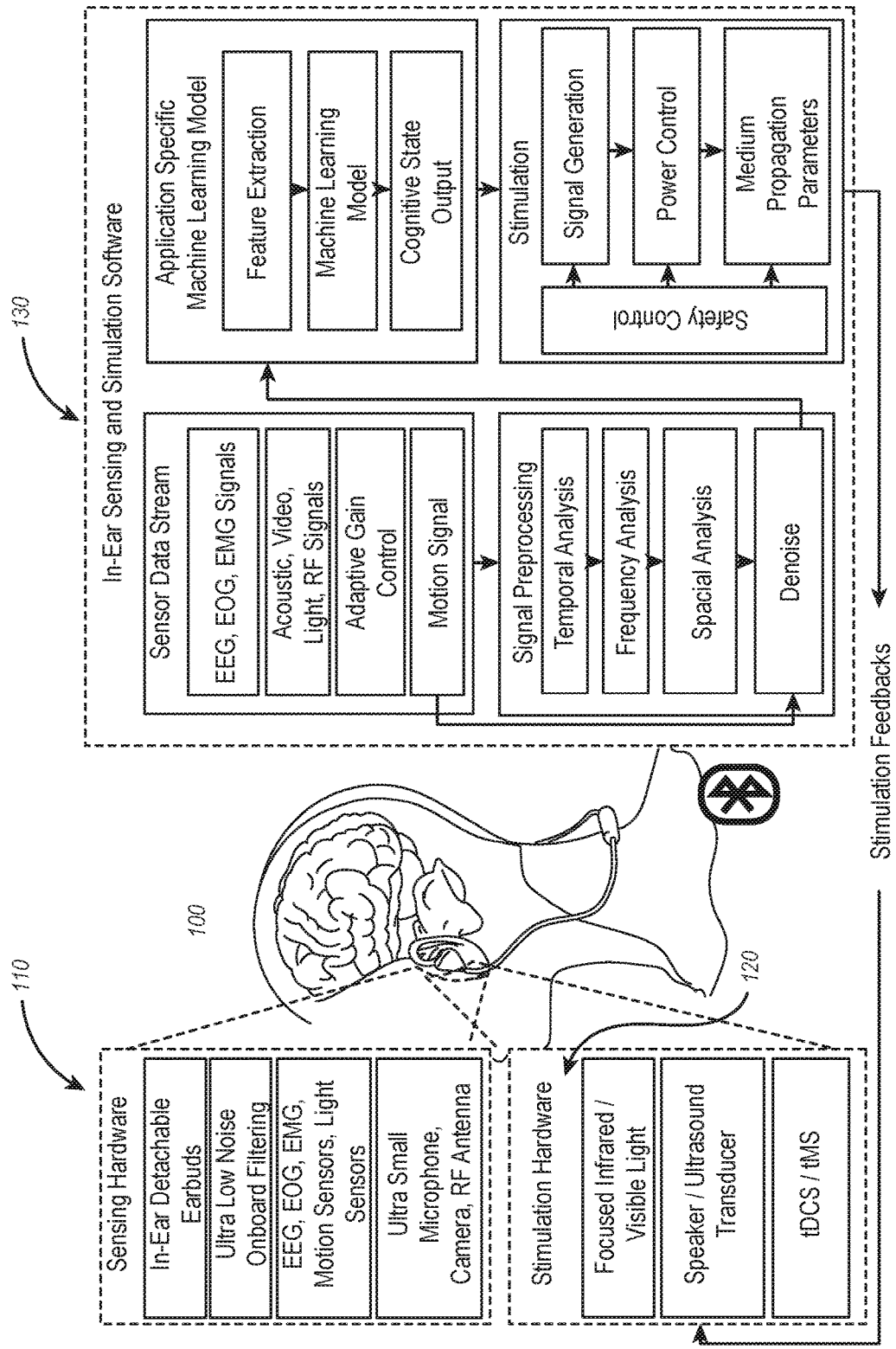
FIG. 1 depicts a schematic diagram of an embodiment of a wearable system for intra-ear sensing and stimulating.

FIG. 1 depicts a schematic diagram of an embodiment of a wearable system 100 for intra-ear sensing and stimulating. The wearable system comprises a pair of in-ear detachable earbud sensors (also referred to herein as "in-ear sensors") that are attached by a cord behind the neck of the user. The wearable system 100 comprises three main components: (1) sensing hardware 110, (2) stimulation hardware 120, and (3) sensing and stimulation control software 130.

In at least one embodiment, the sensing hardware 110 provides on-board analog and digital amplifiers which can amplify small changes of bio-electrical signals and electromagnetic radiation at micro-volt levels with ultra-low internal noises (i.e. <2 uV). In at least one embodiment, the sensing hardware 110 communicates with an off-board computer system such as a mobile phone or external computer. As such, in some embodiments signal processing is performed wholly on-board within the sensing hardware, whereas, in alternative embodiments at least a portion of the signal processing is performed by one or more processors that are external to the sensing hardware.

In at least one embodiment, the in-ear sensor comprises an ultra-small microphone and camera that are integrated within in-ear sensor. The microphone and camera to gather health information in the form of images and various acoustic signals from within the user's ear. The computer system 100 can use this health information to identify physiological variables from the user such as, but not limited to, heart beats, swallowing, and breathing.

In at least one embodiment, the wearable system 100 also comprises stimulation hardware 120. The stimulation hardware 120 provides the wearable system 100 with the ability to notify/warn the user with acoustic signals or to stimulate the deep brain area by using focused light/ultrasound, transcranial direct current or transcranial magnetic stimulation. Accordingly, the wearable system 200 can both receive health data from the in-ear sensor and also provide stimulation to the user using the stimulate hardware 120.

The in-ear sensing and stimulation control software 130 may process the health information captured by the in-ear sensors to remove noises and interference before putting the signals into an application specific machine learning model for feature extractions and classification. After the wearable system 100 generates output on the user's cognitive state, the output is used for stimulation software to generate stimulations back to the user.

Figure 2:
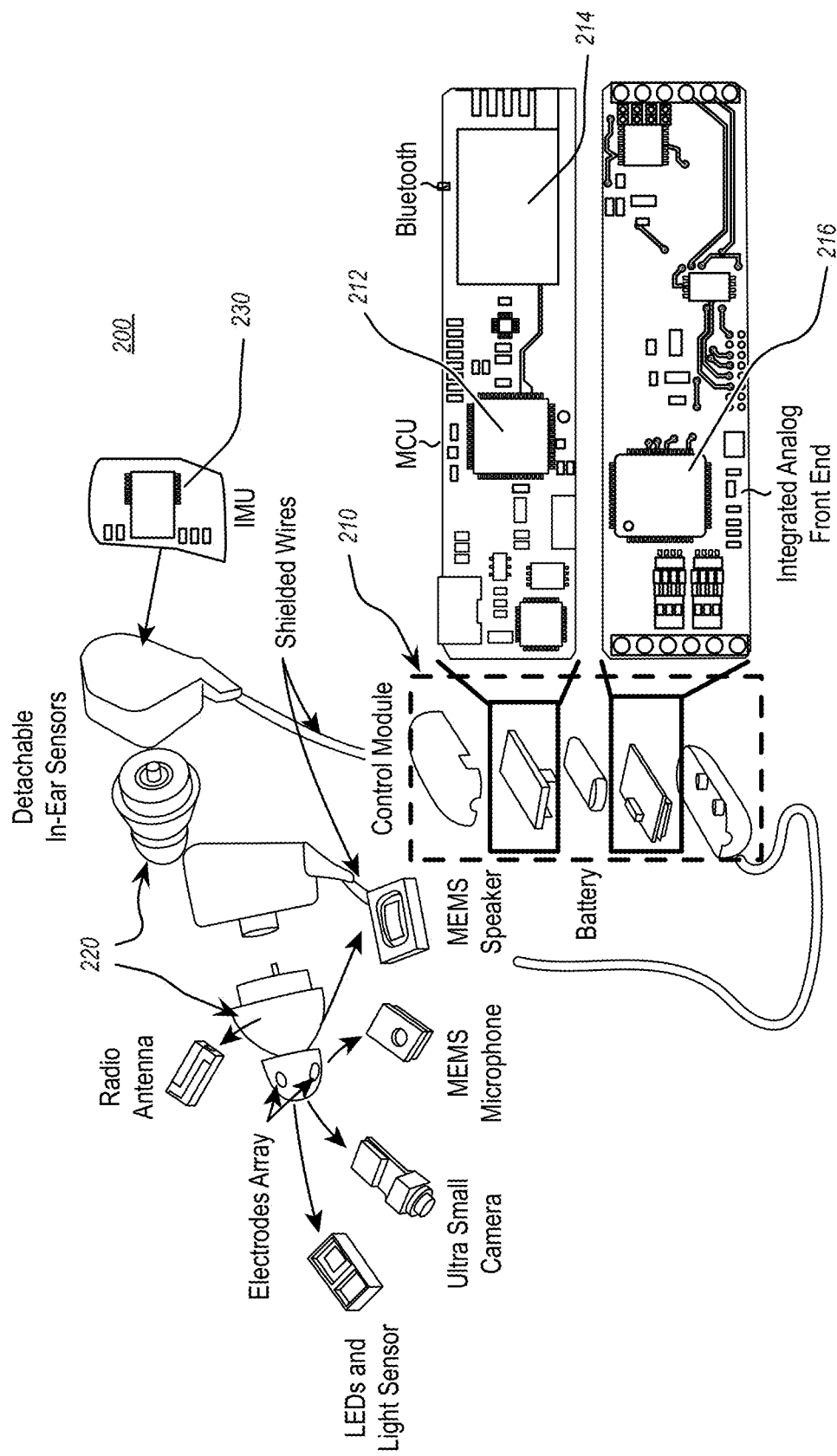
FIG. 2 depicts an exploded view of an embodiment of a wearable system for intra-ear sensing and stimulating.

FIG. 2 depicts an exploded view of an embodiment for a hardware design 200 of a wearable system 100 for intra-ear sensing and stimulating. The depicted embodiment comprises (1) a control module 210 and (2) a pair of in-ear detachable earbud sensors 220. The control module 210 may further comprise a central micro-controller 212 controlling the signal amplifiers circuit and the power system, (2) a Bluetooth module 214 communicating collected signals to a host computer, and (3) an integrated system of signal amplifier and signal generation (i.e. the Integrated Analog Front End 216) capturing sensed signals and generating the stimulations. The whole system can be powered by a rechargeable Li—Po battery placed inside the control module.

In at least one embodiment, the hardware design 200 is configure such that the earbud sensors 220 are detachable from a base member so they can be replaced if necessary. The earbud sensors 220 may hold an array of electronic components for health information sensing and stimulation. For example, in at least one embodiment, the earbud sensors 220 include one or more of the following: an RF antenna, LEDs and light sensor, an inertial measurement unit, an ultra-small camera, a MEMS microphone, and/or a MEMS speaker. Accordingly, the various electronic components within the wearable system 100 can be replaced by attaching replacement earbud sensors 220 to the base member.

Figure 3A:
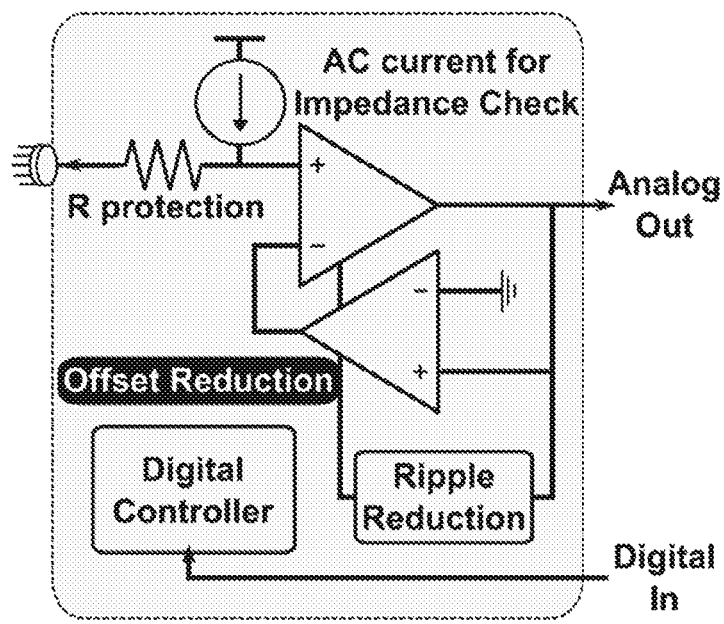
FIG. 3A depicts a schematic of an embodiment of active electrodes.

Additionally, in at least one embodiment, the hardware design 200 comprises in-ear electrodes that extend between both of the user's ears through the cord behind the user's neck. Using the in-ear electrodes the extend between the user's two ears, the wearable system 100 can capture a wide range of brain waves (EEG), eye movements (EOG) and facial muscle contraction (EMG). The in-ear electrodes can be either active electrodes 300, which design is shown in FIG. 3A, or completely passive electrodes.

Figure 4:
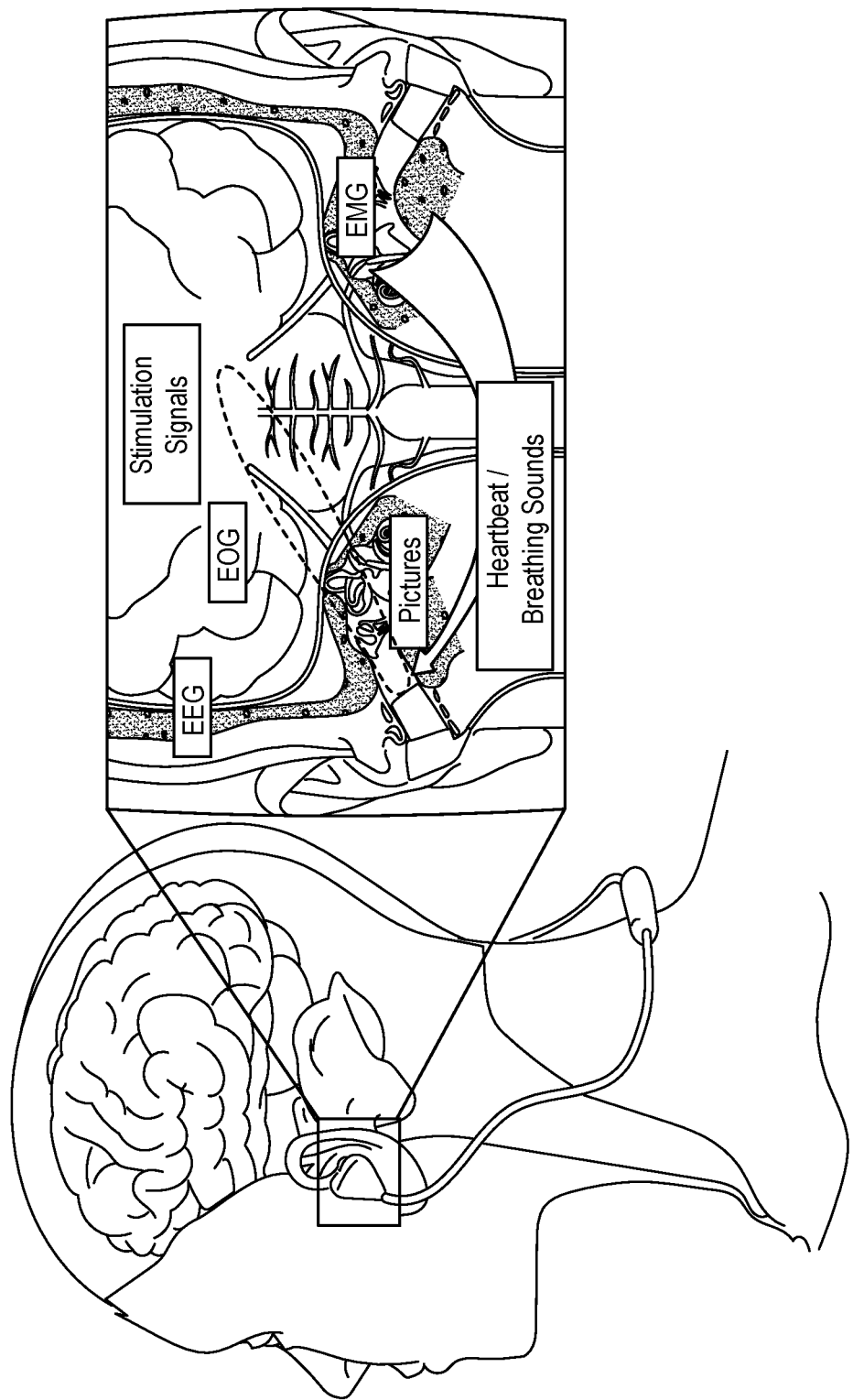
FIG. 4 illustrates embodiments of captured health information and stimulation signals from inside the ear.

In at least one embodiment, a microphone may be facing the ear canal wall so it can pick up the sounds of breathing and heart beating. Additionally, a camera and speaker may be put in the front of the earbud facing the ear drum and the cochlea, so they can effectively capture the images of the ear canal and broadcast acoustic signals to the user. For example, FIG. 4 illustrates the captured health information and stimulation signals from inside the ear.

Figure 3B:
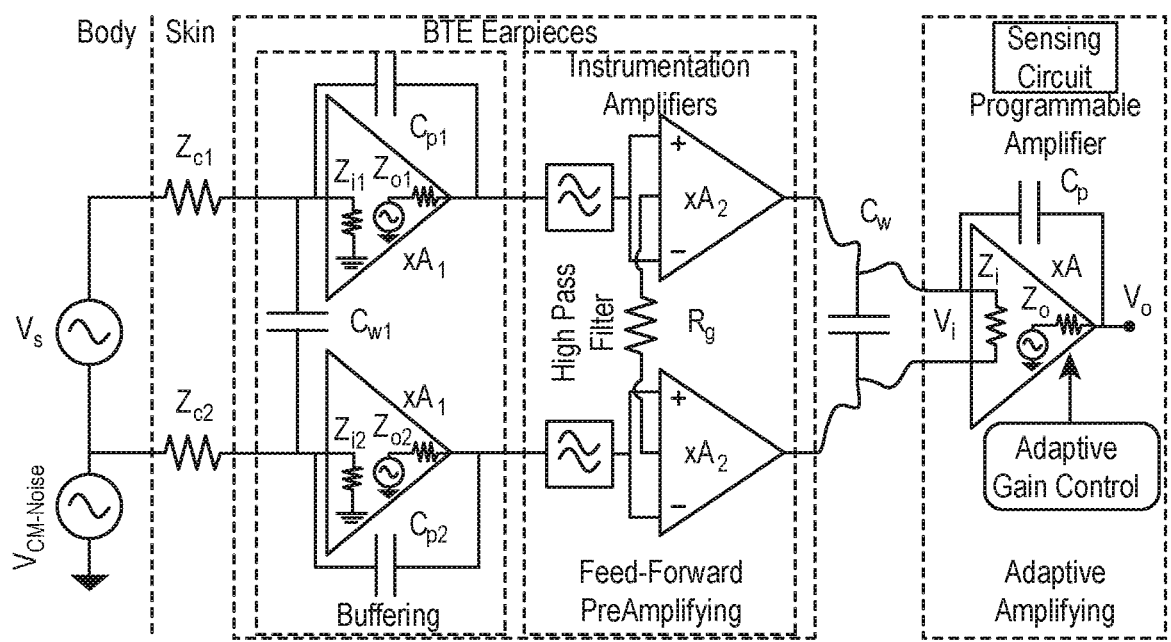
FIG. 3B depicts a schematic of an embodiment of active electrodes with three-fold cascaded amplifying.

FIG. 3B depicts a schematic of an embodiment of active electrodes with three-fold cascaded amplifying. To ensure high fidelity signals, at least one embodiment utilizes three-fold cascaded and amplifying (3CA) on both hardware and firmware levels. FIG. 3B depicts a model for 3CA technique with 3 stages: (1) Stage 1—Buffering, (2) Stage 2—Feed Forward Differential PreAmplifying (F2DP), and (3) Stage 3—Adaptive Amplifying. In at least one embodiment, the first and second stages are implemented in the earpieces while the third stage is implemented on the sensing circuit and its firmware. The 3CA design take into account the unique characteristic of ear-based signals which are (1) weak EEG and EOG signal amplitudes, (2) overlapped signals in both amplitude and frequency, and (3) limited spaces for electrodes.

To reduce the effect of motion artifact created by contact impedance fluctuation and cable sway, the wearable system 100 uses an ultra-high input impedance buffer with unity gain in the first stage. This effectively converts the high impedance signal lines to low impedance ones making it robust to the change of the capacitance on the wires when motion occurs. Conventional systems often place a buffer circuit directly on the electrodes to minimize the inherent capacitance of the signal wires. This may not be desirable as there is limited space for the electrodes. In at least one embodiment, as long as the behind-the-ear sensing system 100 can keep the inherent capacitance small and stable, putting the circuit directly on the electrode is not needed. This is done by shielding the connection between each electrode and its buffer by using a micro-coax shielded cable.

In the second stage, Feed Forward Differential PreAmplifying (F2DP), to ensure robustness against environmental interference, the behind-the-ear sensing system 100 amplifies the weak and overlapped signals before driving the cables to the sensing circuit. Conventional systems typically utilize positive gain and face the challenge with gain mismatch among electrodes because of the difference of contact impedance. By dividing the 3CA into Buffering and F2DP stages, the behind-the-ear sensing system 100 overcomes this challenge because the input impedance of F2DP is effectively close to zero. Thus, the effect of contact impedance will not affect the gain in the next stages. Before preamplifying, the DC component in the signal is removed with a second-order Sallen-Key High Pass Filter so that only the AC signals are amplified.

Additionally, the behind-the-ear sensing system 100 applies a Feed-Forward (FF) differential amplifying technique to further increase Common-Mode Rejection Ratio (CMRR). The behind-the-ear sensing system 100 employs the cross-connection topology where only one gain resistor is needed to set the gain for two FF instrumentation amplifiers in our F2DP. After the F2DP, fully differential and preamplified signals are produced making them robust against environment interference while driving the cables to the sensing circuit.

Within Stage 3 (Adaptive Amplifying), one main challenge that the behind-the-ear sensing system 100 needs to address with the signals is the significant amplitude range differences between the EEG/EOG and the EMG signals. This difference leads to signal saturation at the analog-to-digital converter (ADC) on the sensing circuit when the EMG signal is amplified with the same gain with the EEG/EOG signal. The behind-the-ear sensing system 100 is able to be dynamically adjusted in real-time so that both small EEG/EOG and large EMG signals are captured with high resolution.

This adaptive amplifying can be put either on the earpieces or the sensing circuit or both. In at least one embodiment, the behind-the-ear sensing system 100 implements the adaptive amplifying on the sensing circuit and uses fixed gain amplifiers on the earpieces to preamplify the signal. This reduces the number of wires the behind-the-ear sensing system 100 needs to run from the sensing circuit to the earpieces. Adaptive amplifying may be implemented on the sensing circuit to ensure high quality signals. The behind-the-ear sensing system 100 may utilize a programmable gain instrumentation amplifier controlled by an Adaptive Gain Control (AGC) algorithm.

Figure 3C:
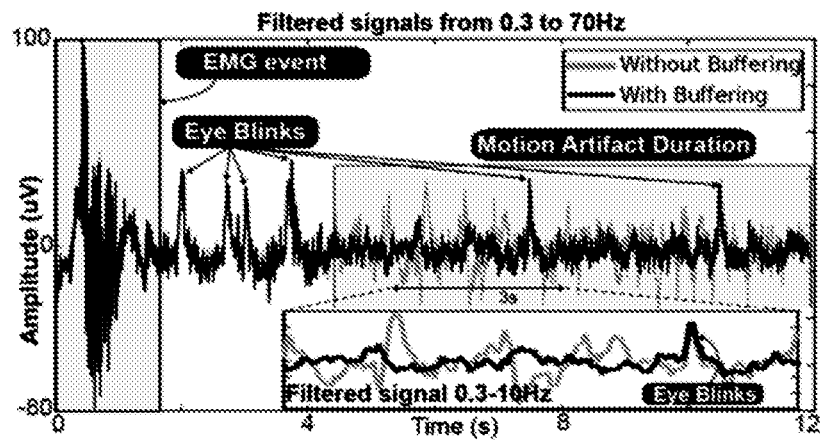
FIG. 3C depicts a graph of an embodiment of filtered signals.
Figure 3D:
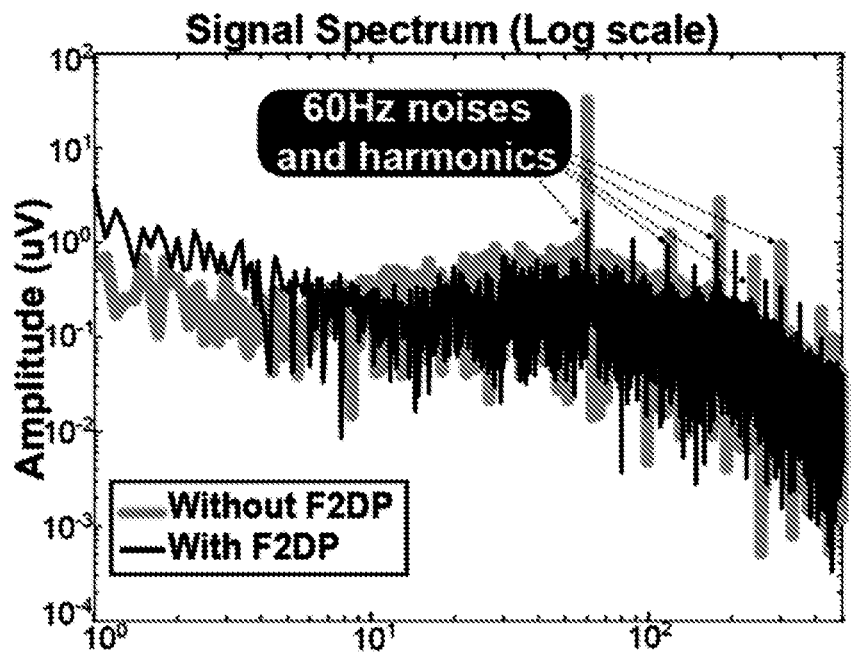
FIG. 3D depicts a graph of an embodiment of a signal spectrum.

FIG. 3C presents the effect of 3CA on suppressing the motion artifact while the user is walking, and the device cables are shaking. As depicted, it is shown that only the motion artifacts are suppressed with 3CA while the same health information is faithfully captured. Without 3CA, the eye blink signals may not be distinguishable from ones created by motions. FIG. 3D shows that with 3CA, electrical line noises (60 Hz) and its harmonics are further suppressed by 24 dB than using DRL alone.

After signals are captured by the earbud sensors 220, they will be further processed by the sensing and stimulation control software 130. The sensing and stimulation control software 130 may be embedded within the control module 210, executed by an external computing device (such as a mobile phone or remote server), or be processed by a combination of the control module 210 and an external computing device. Even though the earbud sensors 220 can sense tiny electrical changes coming from the brain, the eyes and the facial muscle, one of skill in the art will appreciate that there are challenges with signal processing steps before the captured signals can be used, such as signal saturation problems and motion noises mitigation.

In at least one embodiment, to address the difficulties associated with signal saturation problems and motion noises mitigation, a novel technique called "Adaptive Gain Control" (AGC) is utilized for capturing bioelectrical signals such as EEG, EOG and EMG. The 'gain' value, which is how large the signal will be amplified before getting digitalized by an Analog-to-Digital Converter (ADC), can be changed adaptively instead of having a fixed value.

In at least one embodiment, AGC overcomes at least two problems in the art: (1) AGC solves the problem of signal saturation where the amplitude of the DC (direct current) part of the captured signal reaches the maximum dynamic range of the ADC resulting in saturation and no signals being captured. By adaptively changing the gain and adjusting the dynamic range of the ADC, saturation can be avoided. (2) AGC also increase fidelity of the captured signals. Small signals like brainwaves (i.e. EEG), which can be as small as 10 uV, are a thousand times smaller than large signals such as muscle contractions, which can be as strong as 100000 uV. With the disclosed AGC, the system can increase the gain for getting small signals with high resolution, while it can be flexibly and quickly decrease to capture large signals.

One of the main challenges in ensuring high fidelity signals is the large difference in the amplitude range (which could be more than 1000 times) between EEG/EOG and EMG signals. Thus, the analog gain of the sensing circuit needs to adapt dynamically with the changes in signal amplitude. Fortunately, (1) EMG events do not happen frequently, (2) EMG events can happen quickly with strong amplitude changes, and (3) signal amplitude during an EMG events is stochastic and can vary significantly.

Figure 5:
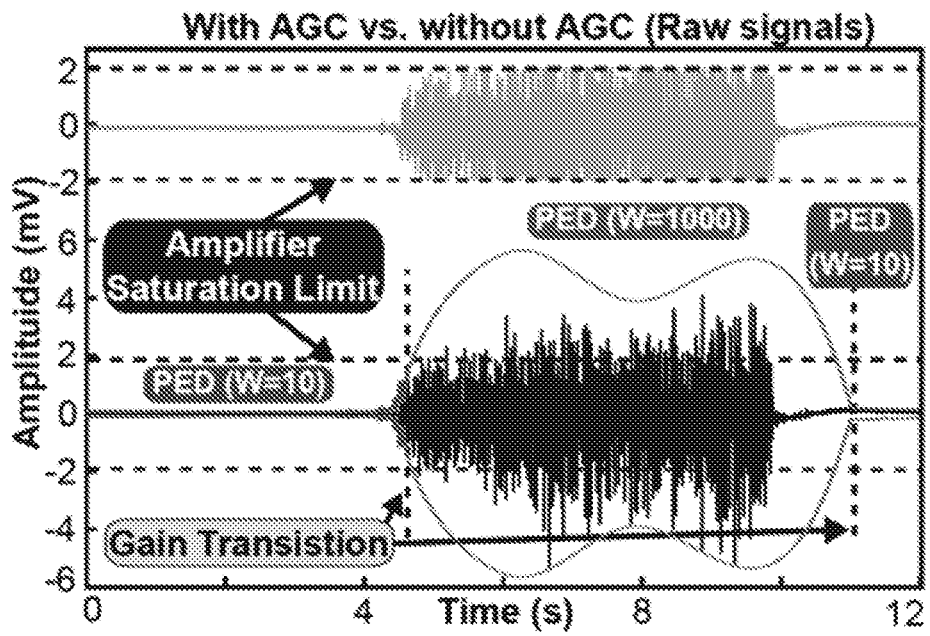
FIG. 5 illustrates charts for embodiments of AGC versus without AGC outcomes.

Understanding these characteristics, the AGC is implemented to (1) keep the gain at a maximum for EEG/EOG signals while there is no significant EMG events, (2) react quickly to the abrupt increase of amplitude to detect EMG events, and (3) react slowly to the decrease of amplitude while an EMG event is still happening to avoid gain oscillation. In at least one embodiment, the wearable system 100 utilizes a dynamic envelope detector such as Peak Envelope (PED) and Square Law (SLD) detectors. The wearable system 100 changes the window size of an envelope detector dynamically so that it can react quickly to a sudden EMG event, while the window size is increased during an EMG event to avoid gain oscillation. AGC is implemented right after oversampling in the sensing circuit firmware to ensure its fast response. The wearable system 100 interpolates missing samples with light-weight linear interpolation. FIG. 5 shows an EMG event could be captured without saturation with AGC.

In at least one embodiment, AGC is implemented in two steps. First, the sensing and stimulation control software 130 repeatedly calculates the exponential moving average (EMA) of a moving window for the captured data. EMA is chosen so that the AGC can react quickly with fast changing signals. Second, the sensing and stimulation control software 130 compares the calculated average with the lower and upper threshold values. If the average is larger than the upper threshold, the sensing and stimulation control software 130 will decrease the gain to extend the dynamic range. In contrast, the sensing and stimulation control software 130 will increase the gain to reduce the dynamic range while increasing the resolution when the average value is smaller than the lower threshold.

The window size, lower and upper threshold may be set at 128 samples, 70% and 90% maximum range of the current gain value, respectively. During a gain transition, several samples may be lost because the amplifier needs to be stabilized before new measurements can be done. Thus, the sensing and stimulation control software 130 can fill in the missing samples by using linear interpolation techniques. Linear interpolation techniques are employed because of their light-weight computational steps.

Figure 6:
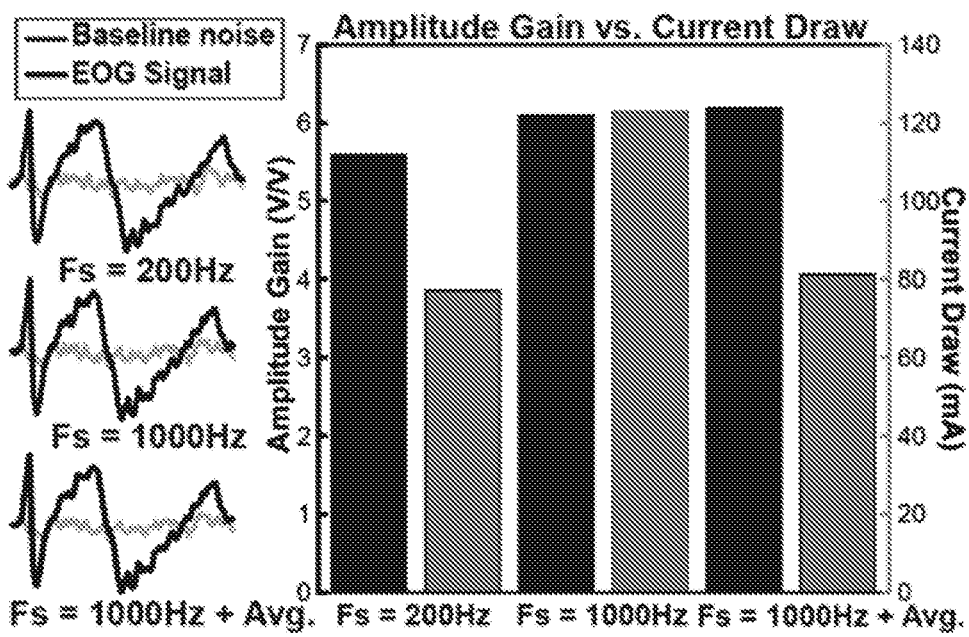
FIG. 6 illustrates charts for amplitude gain versus current draw.

To ensure high signal quality while being power efficient, the wearable system 100 employs oversampling locally on the sensing circuit and down-sampling by taking averages of the collected samples before sending out the average values. Oversampling and averaging (OAA) can improve signal quality by reducing the effect of random noises. Noise sources such as thermal noises, variations in voltage supply, variations in reference voltage, ADC quantization noises could be considered random noises and are reduced with OAA. In addition, oversampling also helps the Adaptive Gain Control to react faster to signal changes. FIG. 6 shows that by using OAA with oversampling rate at 1 kHz and downsample to 200 Hz by averaging, the behind-the-ear sensing system 100 can maintain high SNR while the total current draw of the sensing circuit is cut down.

To mitigate the effect of motion on our captured signals, the system 100 for a wearable system for intra-ear sensing and stimulating employs an inertial measurement unit (IMU) 230 to capture the user's motion. The IMU 230 may be placed directly on the earbud sensors 220 so it can measure the motion affecting the earbud sensors 220. The sensing and stimulation control software 130 may utilize complementary filters to combine the slow-moving signals from an accelerometer and fast-moving signals from a gyroscope. The accelerometer gives a good indicator of orientation in static conditions. The gyroscope gives a good indicator of tilt in dynamic conditions. The sensing and stimulation control software 130 passes the accelerometer signals through a low-pass filter and the gyroscope signals through a high-pass filter and combines them to give the final rate of user's motion. The sensing and stimulation control software 130 then estimates the average power of the angular changes to mitigate the effects of motion by discarding noisy data created by the motions.

The sensing and stimulation control software 130 further processes the captured signals using temporal, frequency, and spatial analysis such as mean removal, median and outlier filtering, bandpass filtering, wavelet decomposition, and independent components analysis before they can be passed to an application specific machine learning model.

Based on the requirements of the application, a set of appropriate features are extracted from the signals. These extracted features are used to classify the user's cognitive state based on different machine learning models such as Support Vector Machine (SVM), K-Nearest Neighbors (KNN), Random Forrest Classifier (RFC), Multi-Layer Perceptron Classifier (MLPC), etc. The output from the model will be used to create stimulation feedbacks. These stimulation feedbacks could be in the form of an acoustic warning, focused infrared light, focused ultrasound, transcranial direct current, or transcranial magnetic stimulation to improve the cognitive quality of the user.

Accordingly, stimulation may be provided through a close-loop model of a system that processes the captured signals from inside the ears, classifies the user's cognitive state with Machine Learning models, and provides stimulation feedbacks to improve user's cognitive condition. Potential cognitive states for monitoring with the earbud sensors 220 includes but are not limited to sleepiness, wakefulness, pain, meditation, focus, ADHD, etc. Stimulation based on electrical, light or acoustic signals can be used to regulate user's cognitive state. For examples, sleepy and wakeful levels can be controlled by exciting or inhibiting the group of orexin neurons in the mid-brain area with electrical signals from the earpieces, thus, the sleep can be induced or prevented when necessary; when the user is in pain, the system can generate relaxing sounds to coach the user's perception of pain.

In at least one embodiment, an application for monitoring epilepsy may be implemented in conjunction with the earbud sensors 220. An epilepsy monitoring application may comprise the ability to capture a wide range of physiological signals while being light-weight and unobtrusive (i.e. hidden inside the ears). The earbud sensors 220 device can be used to continuously monitor seizure activities.

In at least one embodiment, the earbud sensors 220 can extract various features to detect and count seizure activities in real-time. The extracted features may comprise abnormal EEG signals such as spikes, spike-and-low waves, and sharp waves. Typically, the EGG spikes are 20 ms-70 ms in length. The spike-and-slow waves appear after spike waves, and their time length is typically 200 ms-500 ms. Sharp waves are similar to spike-waves, but their time length is typically 70 ms-200 ms.

The extracted features may further comprise a heart rate (HR) and hear rate variability (HRV), which may also change during a seizure and can be used as biomarkers. Studies have shown that HR will increase significantly, which could be more than 100 beats per minute, during seizure. Additionally, seizure patients typically reduce HRV in the interictal state. Moreover, it is also useful to distinguish focal seizures with physical exercise. The extracted features may also comprise muscle contractions, which have been shown to increase during a seizure. Thus, by measuring facial EMG, the wearable system 100 can detect the onset of seizures. Additionally, in at least one embodiment, the extracted features further comprise breathing sounds and body motion, which can be used as complement markers for seizure detection.

By using advanced machine learning models such as Support Vector Machine or Artificial Neural Networks, the activity of seizure can be learnt and identified from the aforementioned features. After seizures are detected, the wearable system 100 can give an early warning through the built-in speaker to the user or provide stimulation therapy. The electrical and magnetic field created by transcranial direct current or transcranial magnetic stimulation can penetrate human tissue painlessly and induces electric currents that can depolarize neurons or axons in the brain reducing the effect of seizure.

Accordingly, disclosure embodiments are capable of utilizing an in-ear earbud sensor system for monitoring and stimulating a user in response to received health information. Such monitoring and stimulating may be performed within feedback loops that automatically adjust and compensation for the received signals.

Figure 7:
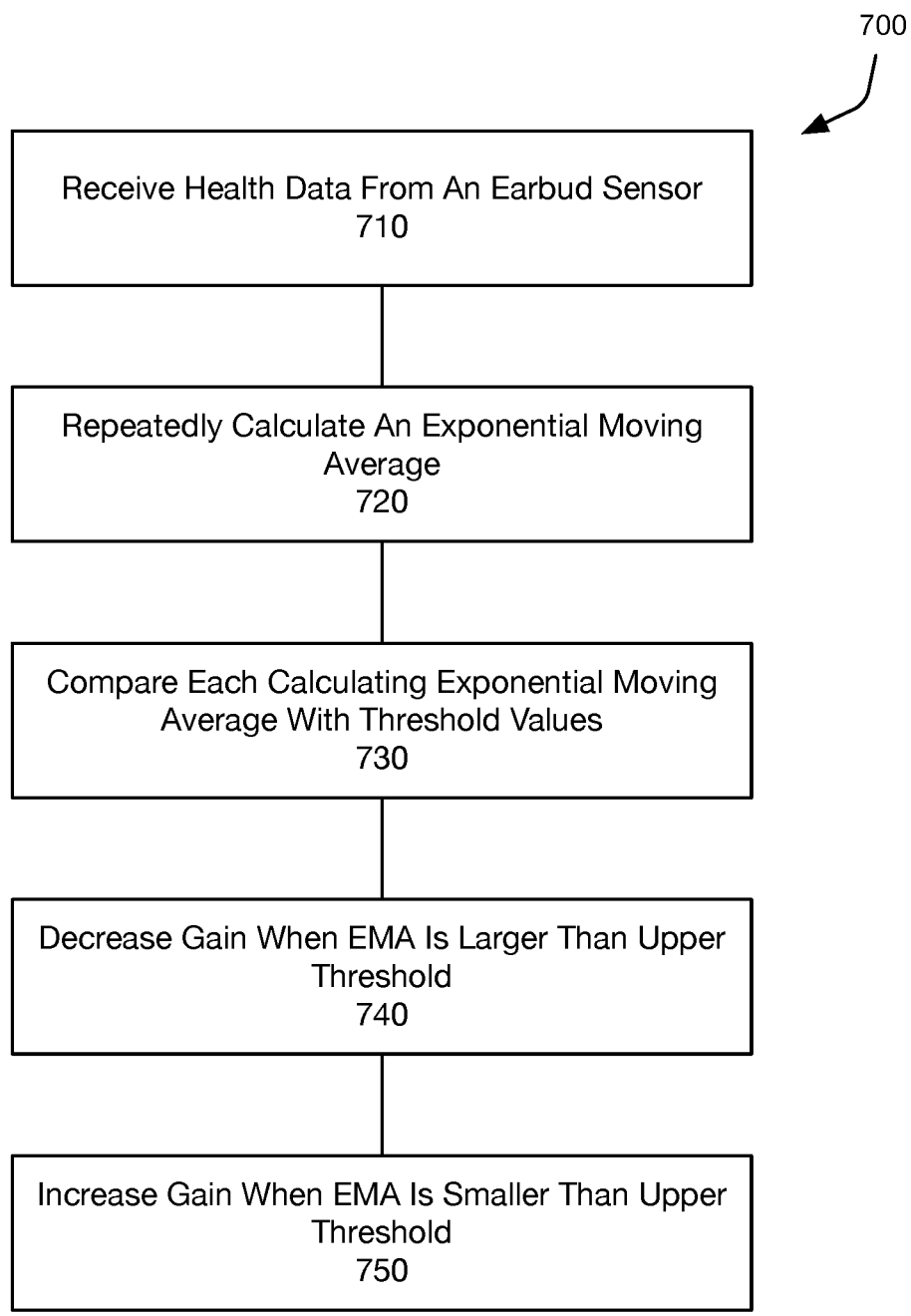
FIG. 7 illustrates a flowchart of a method for intra-ear sensing and stimulating.

FIG. 7 illustrates a flowchart of a method 700 for intra-ear sensing and stimulating. The depicted method includes a step 710 of receiving, health data, from an earbud sensor. The ear bud sensor comprises a shape and size that is configured to extend, at least partially, into an ear canal of a user and one or more of the following sensor components: an inertial measurement unit, an LED and photodiode, a microphone, a radio antenna, or a camera. The method 700 also includes a step 720 of repeatedly calculating an exponential moving average (EMA) of a moving window for the received health data. Additionally, the method 700 includes a step 730 of comparing each calculated exponential moving average with a lower threshold value and an upper threshold value. The upper threshold value and the lower threshold value are determined based, at least in part, upon a saturation level associated within an amplifier performing the adaptive gain control. Further, the method 700 includes a step 740 of when the calculated exponential moving average is larger than the upper threshold, decreasing a gain associated with the amplifier. Further still the method 700 includes a step 750 of when the calculated exponential moving average is smaller than the lower threshold, increasing a gain associated with the amplifier.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Computing system functionality can be enhanced by a computing systems' ability to be interconnected to other computing systems via network connections. Network connections may include, but are not limited to, connections via wired or wireless Ethernet, cellular connections, or even computer to computer connections through serial, parallel, USB, or other connections. The connections allow a computing system to access services at other computing systems and to quickly and efficiently receive application data from other computing systems.

Interconnection of computing systems has facilitated distributed computing systems, such as so-called "cloud" computing systems. In this description, "cloud computing" may be systems or resources for enabling ubiquitous, convenient, on-demand network access to a shared pool of configurable computing resources (e.g., networks, servers, storage, applications, services, etc.) that can be provisioned and released with reduced management effort or service provider interaction. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Cloud and remote based service applications are prevalent. Such applications are hosted on public and private remote systems such as clouds and usually offer a set of web based services for communicating back and forth with clients.

Many computers are intended to be used by direct user interaction with the computer. As such, computers have input hardware and software user interfaces to facilitate user interaction. For example, a modern general purpose computer may include a keyboard, mouse, touchpad, camera, etc. for allowing a user to input data into the computer. In addition, various software user interfaces may be available.

Examples of software user interfaces include graphical user interfaces, text command line based user interface, function key or hot key user interfaces, and the like.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks.

In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

In view of the foregoing the present invention relates for example, without being limited thereto, to the following aspects:

1. A system for intra-ear sensing and stimulating, comprising:
   an earbud sensor comprising:
   a shape and size that is configured to extend, at least partially, into an ear canal of a user, and
   one or more of the following sensor components: an inertial measurement unit, an LED and photodiode, a microphone, a radio antenna, or a camera; and
   wherein the earbud sensor is configured to non-invasively measure various health information, including one or more of brain waves (EEG and electromagnetic fields generated by neural activities), eyes movements (EOG), facial muscle activities (EMG), heart rate, breathing rate, swallowing sound, ear canal pictures, and head motion from inside human ears.

2. The system as recited in any of the preceding aspects, wherein the system is executed in various potential applications in daily life, including one or more of continuous epilepsy monitoring and suppressing, sleep improvements, diagnosing ear infection, memory enhancement, or drug calibration.

3. The system as recited in any of the preceding aspects, wherein the earbud sensor is detachable from a base member such that the earbud sensor can be replaced.

4. The system as recited in any of the preceding aspects, further comprising an in-ear electrical electrode.

5. The system as recited in any of the preceding aspects, wherein the in-ear electrical electrode comprises an active electrode.

6. The system as recited in any of the preceding aspects, wherein the in-ear electrical electrode comprises a passive electrode 7. The system as recited in any of the preceding aspects, wherein the in-ear electrical electrode comprises an array of electrodes.

8. The system as recited in any of the preceding aspects, wherein the in-ear electrical electrode comprises an individual electrode.

9. The system as recited in any of the preceding aspects, further comprising:
   one or more processors; and
   one or more computer-readable media having stored thereon executable instructions that when executed by the one or more processors configure the computer system to perform at least the following:
   repeatedly calculate an exponential moving average (EMA) of a moving window for health information;
   compare each calculated exponential moving average with a lower threshold value and an upper threshold value, wherein the upper threshold value and the lower threshold value are determined based, at least in part, upon a saturation level associated within an amplifier performing the adaptive gain control;
   when the calculated exponential moving average is larger than the upper threshold, decrease a gain associated with the amplifier; and
   when the calculated exponential moving average is smaller than the lower threshold, increase a gain associated with the amplifier.

10. A computer-implemented method, executed on one or more processors, for intra-ear sensing and stimulating, the method comprising:
    receiving, health data, from an earbud sensor, the ear bud sensor comprising:
    a shape and size that is configured to extend, at least partially, into an ear canal of a user, and
    one or more of the following sensor components: an inertial measurement unit, an LED and photodiode, a microphone, a radio antenna, or a camera
    repeatedly calculating an exponential moving average (EMA) of a moving window for the received health data;
    comparing each calculated exponential moving average with a lower threshold value and an upper threshold value, wherein the upper threshold value and the lower threshold value are determined based, at least in part, upon a saturation level associated within an amplifier performing the adaptive gain control;
    when the calculated exponential moving average is larger than the upper threshold, decreasing a gain associated with the amplifier; and
    when the calculated exponential moving average is smaller than the lower threshold, increasing a gain associated with the amplifier.

11. The computer-implemented method as recited in aspect 10, wherein the earbud sensor is detachable from a base member such that the earbud sensor can be replaced.

12. The computer-implemented method as recited in aspects 10 and 11, further comprising an in-ear electrical electrode.

13. The computer-implemented method as recited in aspects 10-12, wherein the in-ear electrical electrode comprises an active electrode.

14. The computer-implemented method as recited in aspects 10-13, wherein the in-ear electrical electrode comprises a passive electrode 15. The computer-implemented method as recited in aspects 10-14, wherein the in-ear electrical electrode comprises an array of electrodes.

16. The computer-implemented method as recited in aspects 10-15, wherein the in-ear electrical electrode comprises an individual electrode.

17. A computer-readable media comprising one or more physical computer-readable storage media having stored thereon computer-executable instructions that, when executed at a processor, cause a computer system to perform a method for intra-ear sensing and stimulating, the method comprising:
    receiving, health data, from an earbud sensor, the ear bud sensor comprising:
    a shape and size that is configured to extend, at least partially, into an ear canal of a user, and
    one or more of the following sensor components: an inertial measurement unit, an LED and photodiode, a microphone, a radio antenna, or a camera
    repeatedly calculating an exponential moving average (EMA) of a moving window for the received health data;
    comparing each calculated exponential moving average with a lower threshold value and an upper threshold value, wherein the upper threshold value and the lower threshold value are determined based, at least in part, upon a saturation level associated within an amplifier performing the adaptive gain control;

when the calculated exponential moving average is larger than the upper threshold, decreasing a gain associated with the amplifier; and when the calculated exponential moving average is smaller than the lower threshold, increasing a gain associated with the amplifier.

18. The computer-readable media as recited in aspect 17, wherein the earbud sensor is detachable from a base member such that the earbud sensor can be replaced.

19. The computer-readable media as recited in aspects 17 and 18, further comprising an in-ear electrical electrode.

20. The computer-readable media as recited in aspects 17-19, wherein the in-ear electrical electrode comprises an active electrode.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for intra-ear sensing and stimulating, comprising:
   an earbud sensor comprising:
      a shape and size that is configured to extend, at least partially, into an ear canal of a user,
      an in-ear electrical electrode, wherein the in-ear electrical electrode comprises an active electrode, and
      a three-fold cascaded amplifier configured to amplify a signal generated by the in-ear electrical electrode, wherein the three-fold cascaded amplifier comprises a buffering stage, a feed forward differential preamplifying stage, and an adaptive amplifying stage;
   one or more processors; and
   one or more physical computer-readable storage media having stored thereon executable instructions that when executed by the e one or more processors configure the system to perform at least the following:
      repeatedly calculate an exponential moving average (EMA) of a moving window for health information;
      compare each calculated exponential moving average with a lower threshold value and an upper threshold value, wherein the upper threshold value and the lower threshold value are determined based, at least in part, upon a saturation level associated within the three-fold cascaded amplifier performing an adaptive gain control;
      when the calculated exponential moving average is larger than the upper threshold value, decrease a gain associated with the three-fold cascaded amplifier;
      when the calculated exponential moving average is smaller than the lower threshold value, increase a gain associated with the three-fold cascaded amplifier; and
   wherein the earbud sensor is configured to non-invasively measure various health information, including one or more of brain waves (EEG and electromagnetic fields generated by neural activities), eyes movements (EOG), facial muscle activities (EMG), heart rate, breathing rate, swallowing sound, ear canal pictures, and head motion from inside human ears.

2. The system as recited in claim 1, wherein the system is executed in various potential applications in daily life, including one or more of continuous epilepsy monitoring and suppressing, sleep improvements, diagnosing ear infection, memory enhancement, or drug calibration.

3. The system as recited in claim 1, wherein the earbud sensor is detachable from a base member such that the earbud sensor can be replaced.

4. The system as recited in claim 1, wherein the in-ear electrical electrode comprises an array of electrodes.

5. The system as recited in claim 1, wherein the in-ear electrical electrode comprises an individual electrode.

6. A computer-implemented method, executed on one or more processors, for intra-ear sensing and stimulating, the method comprising:
   receiving, health data, from an earbud sensor, the earbud sensor comprising:
      a shape and size that is configured to extend, at least partially, into an ear canal of a user,
      an in-ear electrical electrode, wherein the in-ear electrical electrode comprises an active electrode, and
      a three-fold cascaded amplifier configured to amplify a signal generated by the in-ear electrical electrode, wherein a first stage and a second stage of the three-fold cascaded amplifier are implemented in earpieces of the earbud sensor and a third stage of the three-fold cascaded amplifier is implemented on a sensing circuit of the earbud sensor;
   repeatedly calculating an exponential moving average (EMA) of a moving window for the received health data;
   comparing each calculated exponential moving average with a lower threshold value and an upper threshold value, wherein the upper threshold value and the lower threshold value are determined based, at least in part, upon a saturation level associated within the three-fold cascaded amplifier performing an adaptive gain control;
   when the calculated exponential moving average is larger than the upper threshold value, decreasing a gain associated with the three-fold cascaded amplifier; and
   when the calculated exponential moving average is smaller than the lower threshold value, increasing a gain associated with the three-fold cascaded amplifier.

7. The computer-implemented method as recited in claim 6, wherein the earbud sensor is detachable from a base member such that the earbud sensor can be replaced.

8. The computer-implemented method as recited in claim 6, wherein the in-ear electrical electrode comprises an array of electrodes.

9. The computer-implemented method as recited in claim 6, wherein the in-ear electrical electrode comprises an individual electrode.

10. A computer-readable media comprising one or more physical computer-readable storage media having stored thereon computer-executable instructions that, when executed at a processor, cause a computer system to perform a method for intra-ear sensing and stimulating, the method comprising:
   receiving, health data, from an earbud sensor, the earbud sensor comprising:
      a shape and size that is configured to extend, at least partially, into an ear canal of a user,
      an in-ear electrical electrode, wherein the in-ear electrical electrode comprises an active electrode, and
      a three-fold cascaded amplifier configured to amplify a signal generated by the in-ear electrical electrode, wherein a first stage and a second stage of the three-fold cascaded amplifier are implemented in earpieces of the earbud sensor and a third stage of the three-fold cascaded amplifier is implemented on a sensing circuit of the earbud sensor;

comparing each calculated exponential moving average with a lower threshold value and an upper threshold value, wherein the upper threshold value and the lower threshold value are determined based, at least in part, upon a saturation level associated within an three-fold cascaded amplifier performing an adaptive gain control;

when the calculated exponential moving average is larger than the upper threshold value, decreasing a gain associated with the three-fold cascaded amplifier; and when the calculated exponential moving average is smaller than the lower threshold value, increasing a gain associated with the three-fold cascaded amplifier.

11. The computer-readable media as recited in claim 10, wherein the earbud sensor is detachable from a base member such that the earbud sensor can be replaced.

\* \* \* \* \*